US009022997B2

(12) United States Patent
Chung et al.

(10) Patent No.: US 9,022,997 B2
(45) Date of Patent: May 5, 2015

(54) MICRONEEDLE UNIT CAPABLE OF CONTROLLING FLUID DELIVERY

(75) Inventors: Bong Hyun Chung, Daejeon (KR); Nyeon Sik Eum, Daegu (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 111 days.

(21) Appl. No.: 13/263,306

(22) PCT Filed: Apr. 8, 2010

(86) PCT No.: PCT/KR2010/002157
§ 371 (c)(1),
(2), (4) Date: Oct. 6, 2011

(87) PCT Pub. No.: WO2010/117218
PCT Pub. Date: Oct. 14, 2010

(65) Prior Publication Data
US 2012/0059326 A1 Mar. 8, 2012

(30) Foreign Application Priority Data
Apr. 9, 2009 (KR) ........................ 10-2009-0030932

(51) Int. Cl.
*A61M 5/00* (2006.01)
*A61M 37/00* (2006.01)
*A61M 5/178* (2006.01)

(52) U.S. Cl.
CPC ... *A61M 37/0015* (2013.01); *A61M 2037/0023* (2013.01); *A61M 2037/0046* (2013.01); *A61M 2037/0053* (2013.01); *A61M 2037/0061* (2013.10); *A61M 5/178* (2013.01)

(58) Field of Classification Search
USPC .............. 604/272, 274, 21, 173, 164.06, 198, 604/890.1, 30, 33, 181, 246, 249
See application file for complete search history.

(56) References Cited

U.S. PATENT DOCUMENTS

| 6,558,361 | B1 | 5/2003 | Yeshurun |
| 6,780,171 | B2 | 8/2004 | Gabel et al. |
| 8,105,283 | B2* | 1/2012 | Perriere ........................ 604/151 |
| 2007/0088348 | A1* | 4/2007 | Kochamba ..................... 606/41 |
| 2007/0191780 | A1* | 8/2007 | Modi ............................ 604/187 |
| 2008/0108959 | A1 | 5/2008 | Jung et al. |

(Continued)

FOREIGN PATENT DOCUMENTS

| KR | 20-0431404 | 11/2006 |
| KR | 10-0781702 | 12/2007 |

(Continued)

*Primary Examiner* — Aarti B Berdichevsky
*Assistant Examiner* — Laura Schell
(74) *Attorney, Agent, or Firm* — Hammer & Associates, P.C.

(57) ABSTRACT

Provided is a microneedle unit comprising a case having a space accommodating a fluid and a fluid channel through which the fluid is discharged, a microneedle coupled to a lower portion of the case, a base cover disposed at the lower portion of the case, having a hole through which the microneedle passes, and being vertically movable, a guide pin coupled to the base cover and configured to open and close the fluid channel, and an elastic member configured to impart a restoring force such that the base cover is moved upward by an external pressure and then returns downward again. Therefore, the microneedle unit, which is provided to deliver a fluid into the skin with no pain and no scar, can control injection of the fluid using the guide pin, and repeatedly and conveniently control injection of the fluid using the elastic member.

9 Claims, 4 Drawing Sheets

(56) References Cited

U.S. PATENT DOCUMENTS

| | | |
|---|---|---|
| 2009/0163881 A1 | 6/2009 | Jung et al. |
| 2010/0114043 A1 | 5/2010 | Jung et al. |
| 2011/0092883 A1* | 4/2011 | Uchiyama ............... 604/21 |
| 2012/0296280 A1* | 11/2012 | Eum ............... 604/113 |

FOREIGN PATENT DOCUMENTS

| | | |
|---|---|---|
| KR | 10-0792640 | 1/2008 |
| KR | 10-0793615 | 1/2008 |
| KR | 10-2008-0079755 | 4/2009 |

* cited by examiner

MICRONEEDLE UNIT CAPABLE OF CONTROLLING FLUID DELIVERY

CROSS-REFERENCE TO RELATED APPLICATION

This application claims priority to and the benefit of Korean Patent Application No. 2009-0030932, filed Apr. 9, 2009, the disclosure of which is incorporated herein by reference in its entirety.

BACKGROUND

1. Field of the Invention

The present invention relates to a microneedle unit capable of delivering a fluid, and more particularly, to a microneedle unit capable of delivering cosmetics or drugs through the skin tissue, curing the skin tissue, and helping improve a hot-pack effect and skin permeation for improvement of blood circulation.

2. Discussion of Related Art

In general, delivery of cosmetics or drugs through the skin has a disadvantage of a very low absorption rate since the drugs cannot easily pass through a stratum corneum. In particular, when a molecular weight is large, the absorption rate is further reduced. In order to improve this problem, a technique using a microneedle, which may be referred to as a micro stinger, has been proposed.

Fine holes passing through an outer layer or a portion thereof are formed using the microneedle, and the drugs or cosmetics are delivered to the outer layer or a lower layer thereof through the fine holes. In addition, when the microneedle penetrates and stimulates the dermis, a burn or a scar may be naturally cured, and generation of collagen may be induced to maximize skin tone improvement and anti-aging effect.

Korean Utility Model No. 20-0431404 discloses a skin treatment instrument to which a microneedle is attached. In the instrument, when a roller-type apparatus is rolled on the skin after applying nutritional supplement or lotion on the skin, the microneedle forms a micro channel on the skin to stimulate the skin so that the lotion, etc., is evenly distributed to massage the skin surface. However, the instrument may not substantially deliver the drugs into the skin.

In addition, Korean Patent Registration No. 10-0793615 discloses a method of manufacturing a biodegradable solid microneedle including coating a biodegradable viscous material on a substrate surface and drawing the material. In the method, a patch, to which the biodegradable solid microneedle is attached, is applied to the skin to insert the microneedle into the skin. However, in order to deliver the drugs in such a method, treatment drugs must be prepared in the form of a biodegradable viscous material, and there may be irritation caused by foreign matter after insertion into the skin.

Meanwhile, Korean Patent Registration No. 10-0781702 discloses a method of manufacturing a hollow microneedle in consideration of difficulties of drug delivery or body fluid collection through a solid microneedle. While the microneedle manufactured through the method can deliver the drugs into the skin through the hollow microneedle, a vertical movement of the needle is too inflexible to use the needle for curved areas, in particular, a human's face or head, and the needle may be broken due to direct contact with and compression against the skin.

SUMMARY OF THE INVENTION

In order to solve the problems, the present invention is directed to a microneedle unit capable of simply and repeatedly delivering a fluid into the skin, without a separate additional apparatus.

In an aspect, there is provided a microneedle unit comprising: a case having a space accommodating a fluid and a fluid channel through which the fluid is discharged; a microneedle coupled to a lower portion of the case; a base cover disposed at the lower portion of the case, having a hole through which the microneedle passes, and being vertically movable; a guide pin coupled to the base cover and configured to open and close the fluid channel; and an elastic member configured to impart a restoring force such that the base cover is moved upward by an external pressure and then returns downward again.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DESCRIPTION OF THE MARKS

Figure 1:
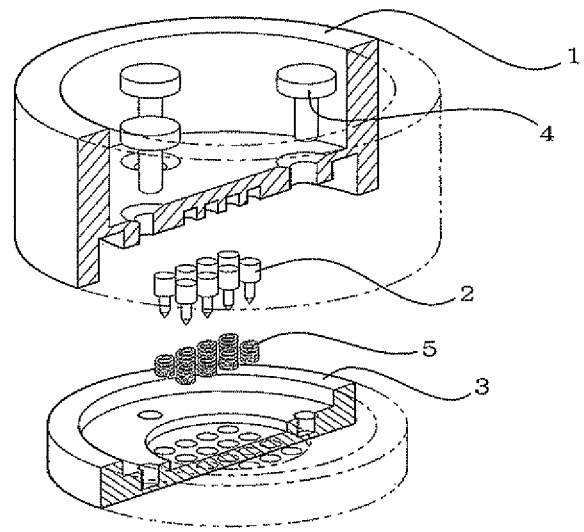
FIG. 1 is a schematic perspective view of a microneedle unit of the present invention.

1: Case
2: Microneedle
3: Base cover
4: Guide pin
5: Spring (Elastic member)
101: Fluid channel
201: Head portion
202: Body portion
203: Insertion portion

BEST MODE FOR CARRYING OUT THE INVENTION

The present invention provides a microneedle unit comprising: a case having a space accommodating a fluid and a fluid channel through which the fluid is discharged; a microneedle coupled to a lower portion of the case; a base cover disposed at the lower portion of the case, having a hole through which the microneedle passes, and being vertically movable; a guide pin coupled to the base cover and configured to open and close the fluid channel; and an elastic member configured to impart a restoring force such that the base cover is moved upward by an external pressure and then returns downward again.

DETAILED DESCRIPTION OF EXAMPLE EMBODIMENTS

Hereinafter, an exemplary embodiment in accordance with the present invention will be described with reference to the accompanying drawings.

Figure 2:
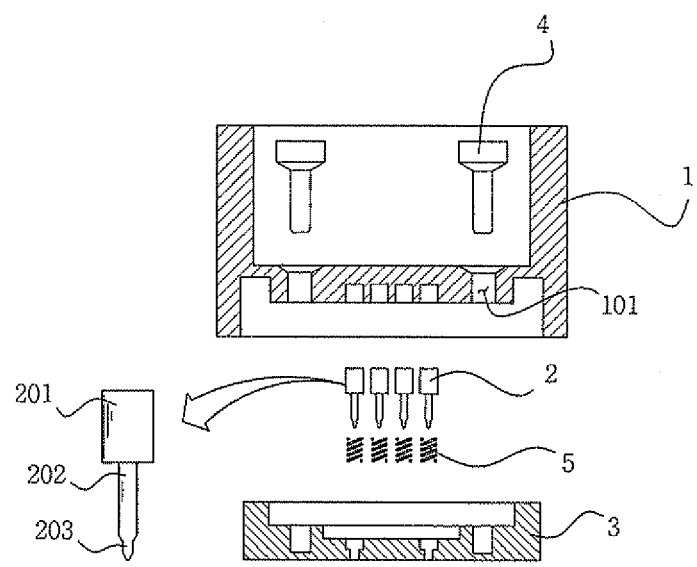
FIG. 2 is a schematic cross-sectional view of the microneedle unit of the present invention.

FIG. 1 is a schematic perspective view of a microneedle unit of the present invention, and FIG. 2 is a schematic cross-sectional view of the microneedle unit of the present invention. The present invention will be described in detail with reference to FIGS. 1 and 2.

In the present invention, 'fluid' means an unshaped material in a liquid or gel phase, having an easy deformable and flowing property. Hereinafter, the term 'fluid' is used with this meaning, and the fluid may be preferably drugs or cosmetics.

A case 1 functions as a fluid chamber containing fluid within a certain space thereof, with an upper portion having an opened entrance trough which the fluid can be introduced from the outside and a lower portion having a fluid channel 101 through which the fluid can be discharged.

The case is not limited to any particular shape and may have a polygonal cross-section, such as circular, triangular, rectangular, pentagonal, hexagonal, octagonal, etc. In a specific example, a microneedle unit having a circular cross-section was manufactured.

The fluid channel formed in the case is not limited to its size and position as long as the fluid can be discharged. In a specific example, the fluid channel may be formed in an edge of the case, or in another specific example, the fluid channel may be formed at a center of the case.

Figure 3:
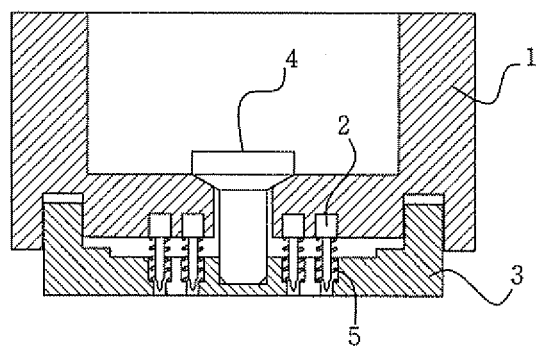
FIG. 3 is a cross-sectional view showing a structure of the microneedle unit of the present invention, in which a guide pin is disposed at a center thereof.

FIG. 2 is a cross-sectional view of the fluid channel formed at the edge of the case, and FIG. 3 is a cross-sectional view of the fluid channel formed at the center of the case.

The case is not limited to any particular material and may be made from polyethylene, polycarbonate, polyvinylchloride, polypropylene, polyetherimide, or the like.

A microneedle 2, which is coupled to the lower portion of the case 1, functions to penetrate the skin to form fine holes.

Here "coupled to" is intended to include attachment or fixation of the microneedle to the lower portion of the case, for example, to a bottom surface of the case, through direct bonding, adhesion, or the like, as well as press-fitting of the microneedle into grooves formed in the bottom surface of the case.

The microneedle 2 is not limited in shape as long as the microneedle can penetrate the skin, and may include a head portion 201, a body portion 202, and an insertion portion 203. The head portion 201 of the microneedle is inserted into a groove formed in the bottom surface of the case, and has a larger diameter than the body portion. The insertion portion 203 is inserted into the skin.

The microneedle is not limited to any particular length and diameter, and the insertion portion 203 is not limited to any particular shape or outer diameter, as long as it is within a range of causing no pain when the insertion portion 203 is inserted into the skin. Preferably, the outer diameter may be within a range of 1 µm to 100 µm, and a tip of the insertion portion may be ground to an angle of 37° to 44°.

While the microneedle is not limited to a particular material as long as the material is used in the art, the microneedle may be manufactured using acryl, polyacrylate, polycarbonate, epoxy, polyester, polyetheretherketone, polyvinyl chloride, polyolefin, liquid crystal polyester, or a resin composition synthesized from any of these materials, or may be manufactured using a solid material including stainless steel or another metal.

The base cover 3 functions to guide the microneedle, and is disposed under the case 1 and designed to be vertically movable.

The base cover 3, which is a portion that contacts the surface of the skin, has a plurality of holes, through which the microneedle 2 can pass, corresponding to the number and position of microneedles. The base cover 3 is moved under the microneedle such that the microneedle does not project when no external pressure is applied, and the base cover 3 moves upward when the external pressure is applied such that the microneedle projects to an extent to which the skin is penetrated.

Figure 4:
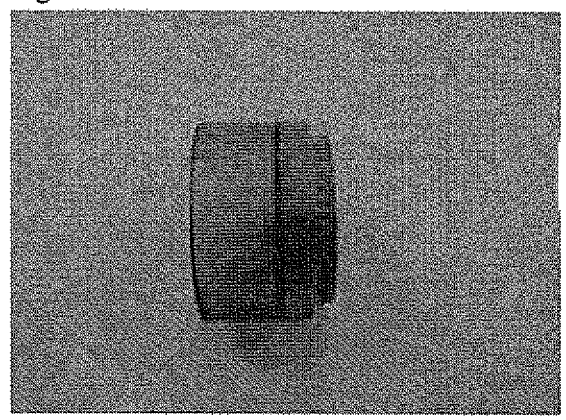
FIG. 4 is a side view showing a structure of the microneedle unit of the present invention, in which a base cover is formed at a case in a stepped shape.

In addition, in a specific example, in order to make a front surface of the base cover easily contact the skin, the base cover may be formed at the case in a stepped shape, as shown in FIG. 4.

The base cover is not limited to a particular material as long as the material is used in the art, but may be formed of polyethylene, polycarbonate, polyvinylchloride, polypropylene, or polyetherimide.

The guide pin 4 functions to open and close the fluid channel of the case 1, and is coupled to the base cover 3.

The portion of the base cover coupled to the guide pin is a rear surface thereof opposite to the front surface when a portion that contacts the surface of the skin is seen as the front surface. Hereinafter, the portion of the base cover that contacts the surface of the skin is referred to as the front surface, and the surface opposite thereto is referred to as the rear surface.

Here, "coupled to" is intended to include attachment or fixation of the guide pin to the rear surface of the base cover through direct bonding, adhesion, or the like, as well as press-fitting of the guide pin into grooves formed in the rear surface of the base cover.

The guide pin 4 is not limited to any particular shape as long as the pin can open and close the fluid channel of the case 1. In a specific example, the guide pin has a T-shaped cross-section. A horizontal portion of the T shape has a greater width than the fluid channel of the case to close an outlet of the fluid channel with open armed-shape, and a vertical portion of the T shape has a smaller width than the fluid channel of the case to pass through the fluid channel. A tip of the vertical portion is coupled to the rear surface of the base cover to prevent separation of the base cover from the case.

The guide pin may be appropriately sized according to the size of the case, and the diameter and length of the horizontal and vertical portions are not particularly limited.

The guide pin is not limited to any particular material as long as the material is used in this art, but the guide pin may be manufactured using a solid material such as stainless steel or another metal. Preferably, the manufactured guide pin may be plated with gold.

An elastic member 5, which is disposed between the case 1 and the base cover 3, functions to impart a restoring force such that the base cover 3 is moved upward by an external pressure and then returns downward.

The elastic member is not limited to any particular material and shape as long as the elastic member can provide a restoring force such that the base cover is moved upward by an external pressure and then returns downward. In a specific example, the elastic member may be a spring.

The elastic member is not limited to any particular material as long as the material is used in this art, but the elastic member may be manufactured using a solid material including stainless steel or another metal. Preferably, the manufactured guide pin may be plated with gold.

Since the microneedle unit of the present invention has the case 1 with the upper portion opened, for example, the upper portion of the case 1 may be manufactured to be press-fitted into a vial (ample) vessel, in which a fluid is contained. The microneedle unit may be repeatedly used by refilling the vial (ample) vessel when the fluid is exhausted.

Figure 5:
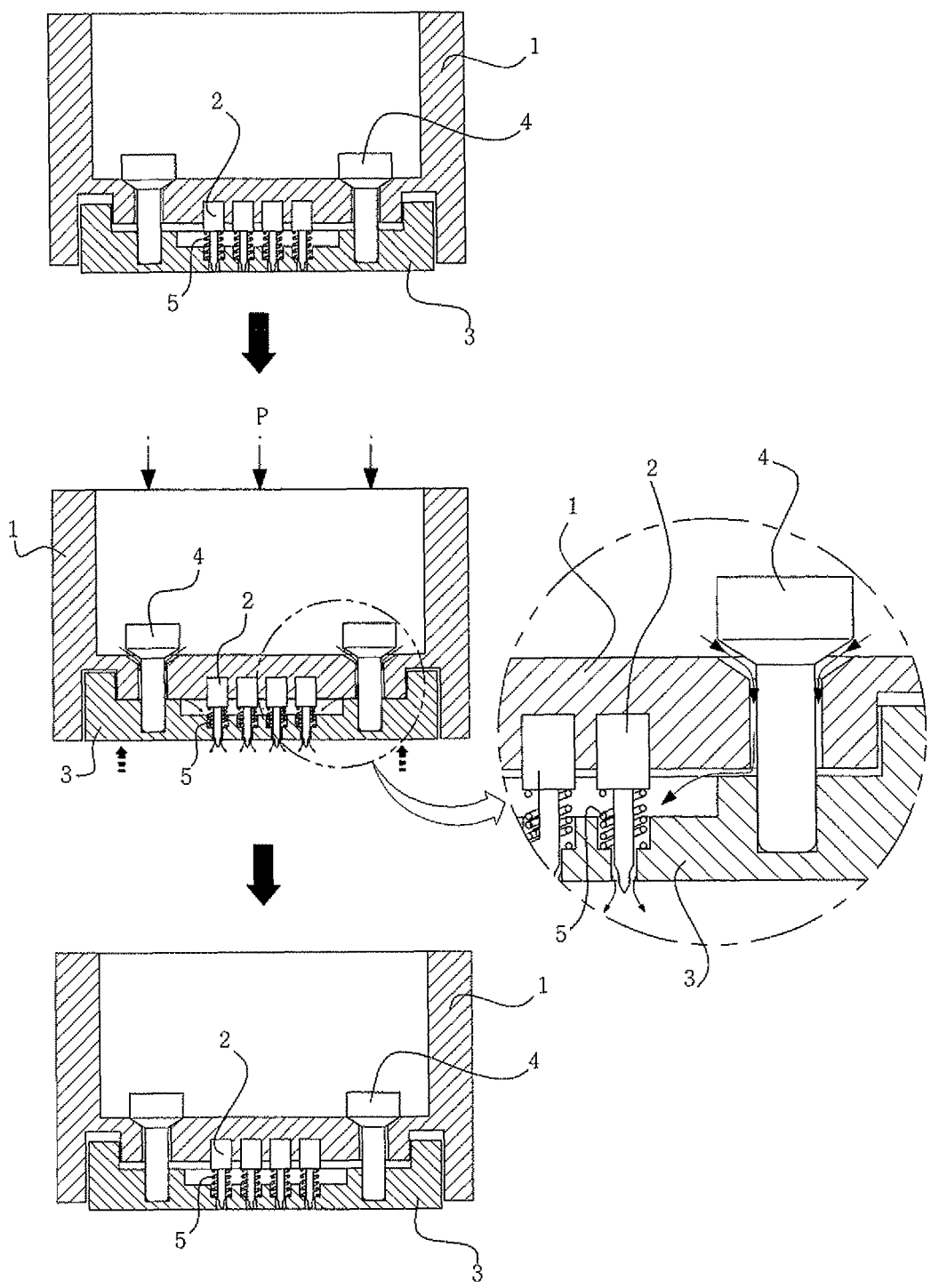
FIG. 5 is a cross-sectional view schematically showing a process of opening a fluid channel of the case after the base cover of the microneedle unit of the present invention is moved upward by an external pressure.

Referring FIG. 5 and describing an operation of the microneedle unit according to the present invention, after bringing the base cover 2 into contact with the skin, an external pressure is applied to the upper portion of the case 1 and the base cover 3 moves upward. When the base cover 3 moves upward, the microneedle 2 penetrates the skin through the hole of the base cover 3. At the same time the microneedle 2 penetrates the skin, the guide pin 4 moves upward to open the fluid channel 101, and the fluid is delivered into the skin through the open fluid channel. Then, when the external pressure pushing the upper portion of the case 1 is removed, the base cover 3 is moved downward by the recovery force of the elastic member 5, and simultaneously, the guide pin 4 moves downward to close the fluid channel 101.

The present invention provides an array including the microneedle unit.

Accordingly, a plurality of microneedle units according to the present invention may be arrayed, and thus, a portable device such as a comb, a brush, and a cotton ball may be manufactured using an array of microneedle units.

Figure 6:
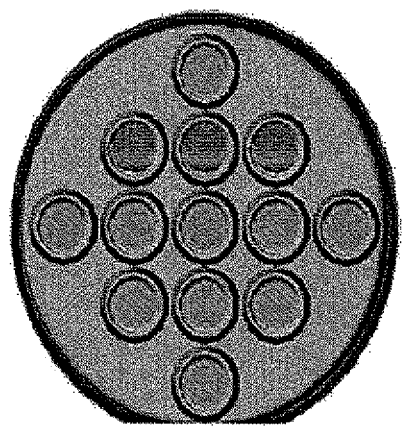
FIG. 6 is an image of a microneedle brush, in which 13 microneedle units are integrated to be applied to the head or skin.

FIG. 6 is a photograph of a microneedle brush in which 13 microneedle units according to the present invention are integrated to be applied to the head or skin.

In addition, the present invention provides a syringe including the microneedle unit.

As can be seen from the foregoing, the microneedle unit of the present invention can control injection of a fluid using the guide pin, and repeatedly and conveniently control injection of the fluid using the elastic member.

While the invention has been shown and described with reference to certain example embodiments thereof, it will be understood by those skilled in the art that various changes in form and details may be made therein without departing from the spirit and scope of the invention as defined by the appended claims.

What is claimed is:

1. A microneedle unit comprising:
a case having a space accommodating a fluid and a fluid channel through which the fluid is discharged;
a microneedle coupled to a lower portion of the case;
a base cover coupled with the lower portion of the case by a guide pin, having a hole through which the microneedle passes, and being vertically movable;
the guide pin including a horizontal portion that has a greater width than the fluid channel to be able to close an outlet of the fluid channel, a vertical portion which has a smaller width than the fluid channel and passes through the fluid channel whereby one side of the vertical portion is connected to the horizontal portion, and the other side of the vertical portion, which is coupled to the base cover and configured to open and close the fluid channel by the vertical movement of the base cover; and
an elastic member configured to impart a restoring force such that the base cover is moved upward by an external pressure and then returned downward again.

2. The microneedle unit according to claim 1, wherein the fluid channel of the case, through which the fluid is discharged, is formed at an edge of the case.

3. The microneedle unit according to claim 1, wherein the fluid channel of the case, through which the fluid is discharged, is formed at a center of the case.

4. The microneedle unit according to claim 1, wherein the guide pin has a T-shaped cross-section.

5. The microneedle unit according to claim 1, wherein the elastic member is a spring.

6. The microneedle unit according to claim 1, wherein the base cover is formed at the case in a stepped shape.

7. An array comprising the microneedle unit according to any one of claims 1 to 6.

8. A microneedle brush comprising the microneedle unit according to any one of claims 1 to 6.

9. A syringe comprising the microneedle unit according to any one of claims 1 to 6.

* * * * *